Figure 1:
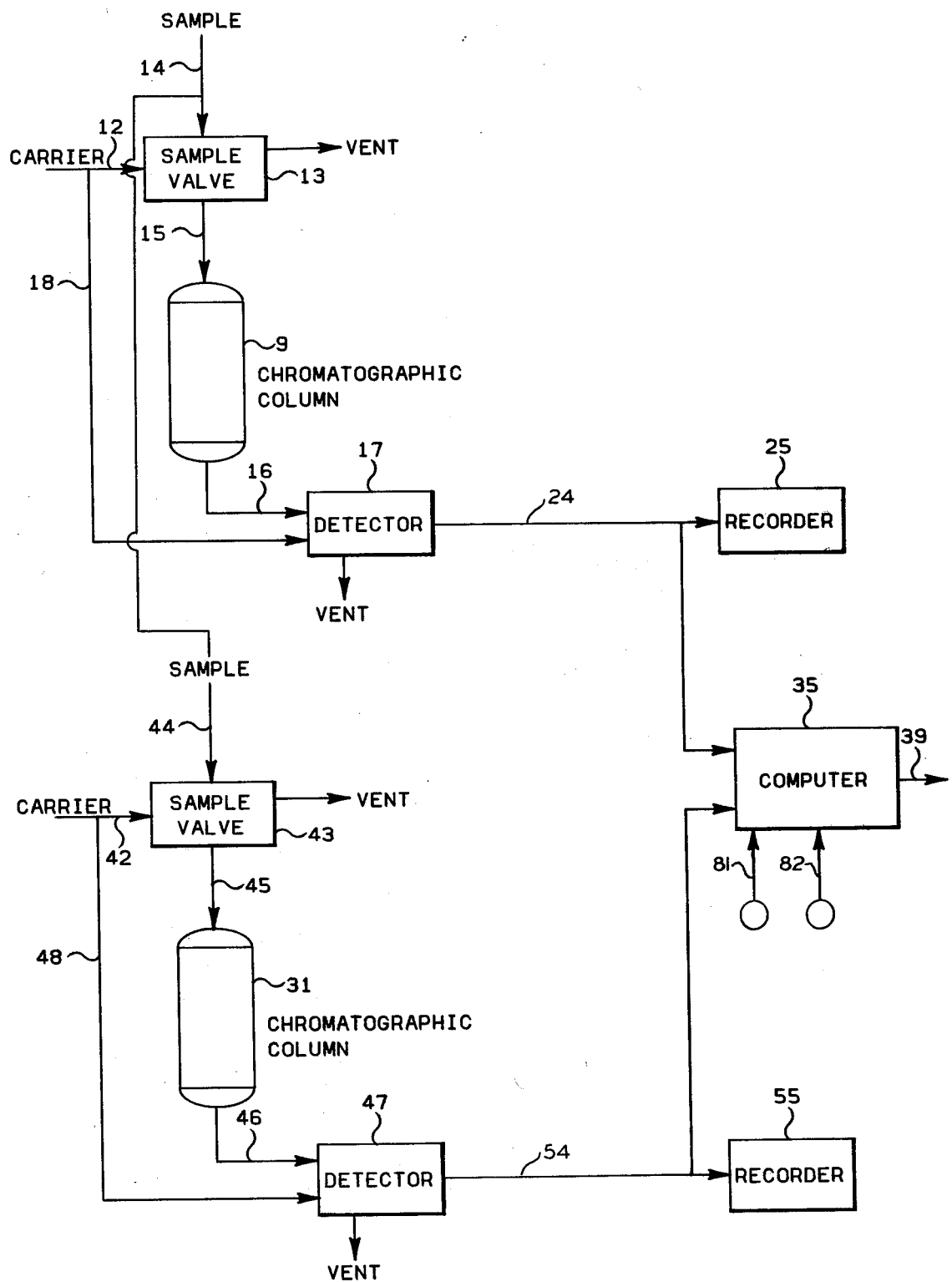

United States Patent [19]

DeFord

[11] 4,181,006
[45] Jan. 1, 1980

[54] QUANTITATIVE CHROMATOGRAPHIC ANALYSIS WITHOUT CALIBRATION

[75] Inventor: Donald D. DeFord, Evanston, Ill.

[73] Assignee: Phillips Petroleum Company, Bartlesville, Ohio

[21] Appl. No.: 938,588

[22] Filed: Aug. 31, 1978

[51] Int. Cl.² .................................... G01N 31/08
[52] U.S. Cl. ........................................... 73/23.1
[58] Field of Search ............. 73/23.1, 1 G; 23/232 C; 422/89

[56] References Cited

U.S. PATENT DOCUMENTS

| | | | |
|---|---|---|---|
| 2,868,216 | 1/1959 | Robertson | 356/130 |
| 3,408,854 | 11/1968 | Larson | 73/23.1 |
| 3,585,002 | 6/1971 | Boys | 73/23.1 |
| 3,674,373 | 7/1972 | Waters et al. | 356/130 |

Primary Examiner—Stephen A. Kreitman

[57] ABSTRACT

A quantitative analysis of the concentration of the individual components in a sample is obtained using a chromatographic analyzer without the need to calibrate the chromatographic analyzer detector. Two chromatographic analyzer systems are utilized to analyze two identical samples using two different carrier fluids. The difference in the response of the two chromatographic analyzers is proportional to the difference in the properties of the two carrier fluids being measured by the Chromatographic analyzer detectors and the concentration of the desired component of the sample. Because the proportionality does not involve the property of the individual sample component being measured by the chromatographic analyzer detector, it is possible to obtain a quantitative analysis of the concentration of the individual components of the sample without the need to calibrate the chromatographic analyzer detectors.

14 Claims, 2 Drawing Figures

QUANTITATIVE CHROMATOGRAPHIC ANALYSIS WITHOUT CALIBRATION

This invention relates to chromatography. In a specific aspect this invention relates to method and apparatus for obtaining a quantitative analysis of the concentration of an eluted component without the necessity of calibrating a chromatographic analyzer detector.

A chromatographic analyzer is an analytical instrument that is used to separate in time and individually detect the constituents of a sample to be analyzed. The chromatographic analyzer typically includes an analytical column through which a carrier fluid is passed continuously. The sample to be analyzed is injected into the carrier stream and is thus carried through the analytical column. The sample constituents are carried through the analytical column at different velocities and in this manner the sample constituents are separated in time.

A detector is employed to detect the separated constituents and the detector output signal typically is plotted as a function of time to produce what is termed a chromatogram. As each sample component is eluted from the column the component produces a sharp increase in the detector output signal amplitude, which increase appears as a peak or spike in the chromatogram.

The response of a chromatographic analyzer detector such as a refractive index detector or a thermal conductivity detector is given by $$R = KC_z(N_z - N) \tag{I}$$

where
R = detector response,
K = detector sensitivity constant,
$C_z$ = concentration of the component z,
$N_z$ = the measurable property of the component z, and
N = the same measurable property for the carrier fluid.

In the case of a refractive index detector, $N_z$ would be representative of the refractive index of the component z and N would be representative of the refractive index of the carrier fluid. In the case of a thermal conductivity detector, $N_z$ would be representative of the thermal conductivity of the component z and N would be in like manner representative of the thermal conductivity of the carrier fluid.

It is apparent from equation (I) that unless the measurable property, such as the refractive index, of the individual components of the sample is known or the chromatographic analyzer detector can be calibrated with a known amount of the pure components, that a quantitative measure of the concentration of the individual components of the sample cannot be obtained from the detector response because the detector response is related to both the concentration of the individual components and the measurable property of the individual components. Often the response of the measurable property of the individual components of the sample is not known and a pure compound is not available for calibration of the chromatographic analyzer detectors. In the past, when these conditions occurred, it was not possible to obtain a quantitative analysis of the concentration of the individual components in the sample when a chromatographic analyzer detector having the response given by equation (I) was used in the chromatographic analyzer system.

Accordingly, it is an object of this invention to provide method and apparatus for obtaining a quantitative analysis of the concentration of an eluted component without the necessity of calibrating a chromatographic analyzer detector.

In accordance with the present invention, method and apparatus is provided whereby separate chromatographic analyzer systems are preferably utilized to obtain a quantitative analysis of the concentration of the individual components in a sample without the necessity of calibrating the chromatographic analyzer detector. The operating characteristics of the two chromatographic analyzer systems are similar and every effort is made to maintain factors such as flow rates and sample sizes identical in both systems. A single chromatographic analyzer system could be utilized, but two separate chromatographic analyzer systems are preferred. It would be necessary to perform two chromatographic analyses at different times if only a single chromatographic analyzer system is utilized.

Identical samples are analyzed in both chromatographic analyzer systems with each chromatographic analyzer system utilizing a different carrier fluid. The different carrier fluids have different properties which can be measured by the chromatographic analyzer detector. Properties such as the refractive index of the carrier fluid, the thermal conductivity of the carrier fluid, or the dielectric constant of the carrier fluid are commonly measured. The carrier fluids are chosen so that the elution time of the individual components in the sample will be the same in both chromatographic analyzer systems or the individual components of the sample will be completely resolved in the chromatographic analyzer outputs of both chromatographic analyzer systems.

The chromatographic analyzer detector response for a component run with a first carrier fluid is given by $$R_1 = KC_z(N_z - N_1) \tag{II}$$

where
$R_1$ is the detector response of a chromatographic analyzer to the component run with the first carrier fluid,
$C_z$ is the concentration of component z,
$N_z$ is the measurable property of component z,
$N_1$ is the same measurable property of the first carrier fluid, and
K is a detector constant associated with the sensitivity of the chromatographic analyzer detector.

The chromatographic analyzer detector response for a component run with the second carrier fluid is given by $$R_2 = KC_z(N_z - N_2) \tag{III}$$

where
$R_2$ is the detector response of a chromatographic analyzer,
$N_2$ is the measurable property of the second carrier fluid, and
$C_z$, $N_1$ and K are as previously defined.

If two chromatographic analyzer systems are used then the constant K may not be equal for both detectors. Letting $K_1$ equal the detector constant associated with the sensitivity of the first chromatographic analyzer detector and $K_2$ equal the detector constant associated with the sensitivity of the second chromatographic analyzer detector, equation II becomes $$R_1 = K_1 C_z (N_z - N_1) \qquad \text{(IV)}$$

and equation III becomes $$R_2 = K_2 C_z (N_z - N_2) \qquad \text{(V)}$$

The difference in responses for the two chromatographic analyzers using two different carrier fluids is given by $$R_1 - \frac{K_1}{K_2} R_2 = K_1 C_z (N_2 - N_1) \qquad \text{(VI)}$$

or $$C_z = \frac{R_1 - \frac{K_1}{K_2} R_2}{K_1 (N_2 - N_1)} \qquad \text{(VII)}$$

For any two carrier fluids $(N_2 - N_1)$ will be a constant. Thus, equation VII can be simplified to $$C_z = \frac{R_1 - k_1 R_2}{k_2} \qquad \text{(VIII)}$$

where
$k_1$ is equal to $K_1/K_2$,
$k_2$ is equal to $K_1(N_2 - N_1)$, and
$C_z$, $R_1$ and $R_2$ are as previously defined.
Equation VIII may be rewritten as $$C_z = k_3 R_1 - k_4 R_2 \qquad \text{(IX)}$$

where
$k_3$ is equal to $1/k_2$,
$k_4$ is equal to $k_1/k_2$, and
$C_z$, $R_1$ and $R_2$ are as previously defined.

It can be seen from equation IX that the concentration of the desired component is proportional to the difference in the response of the two chromatographic analyzers. Since the responses $R_1$ and $R_2$ of the two chromatographic analyzers are known and the constants $k_3$ and $k_4$ can be easily established, it is a simple matter to solve equation IX for the concentration of the desired component.

It should be noted that equation IX does not involve the measurable property of the component being analyzed, so this parameter need not be known to do a quantitative analysis. In fact, it is clear from equation IX that the differential response of the two chromatographic analyzers is the same for any sample component regardless of the response given by the measurable property of the sample components. Thus, the calibration factor for every component in a sample is identical.

If a single chromatographic analyzer system is used, then the difference in the separate responses of the single chromatographic analyzer using two different carrier fluids is given by $$R_1 - R_2 = K C_z (N_2 - N_1). \qquad \text{(X)}$$

Equation X could be simplified to $$C_z = (R_1 - R_2/k) \qquad \text{(XI)}$$

where
k is equal to $K(N_2 - N_1)$ because $(N_2 - N_1)$ will be a constant.

It can be seen from equation XI that the concentration of the desired component is proportional to the difference in the separate responses of the single chromatographic analyzer system. Again, equation XI does not involve the measurable property of the component being analyzed and this parameter need not be known to do a quantitative analysis.

Figure 2:
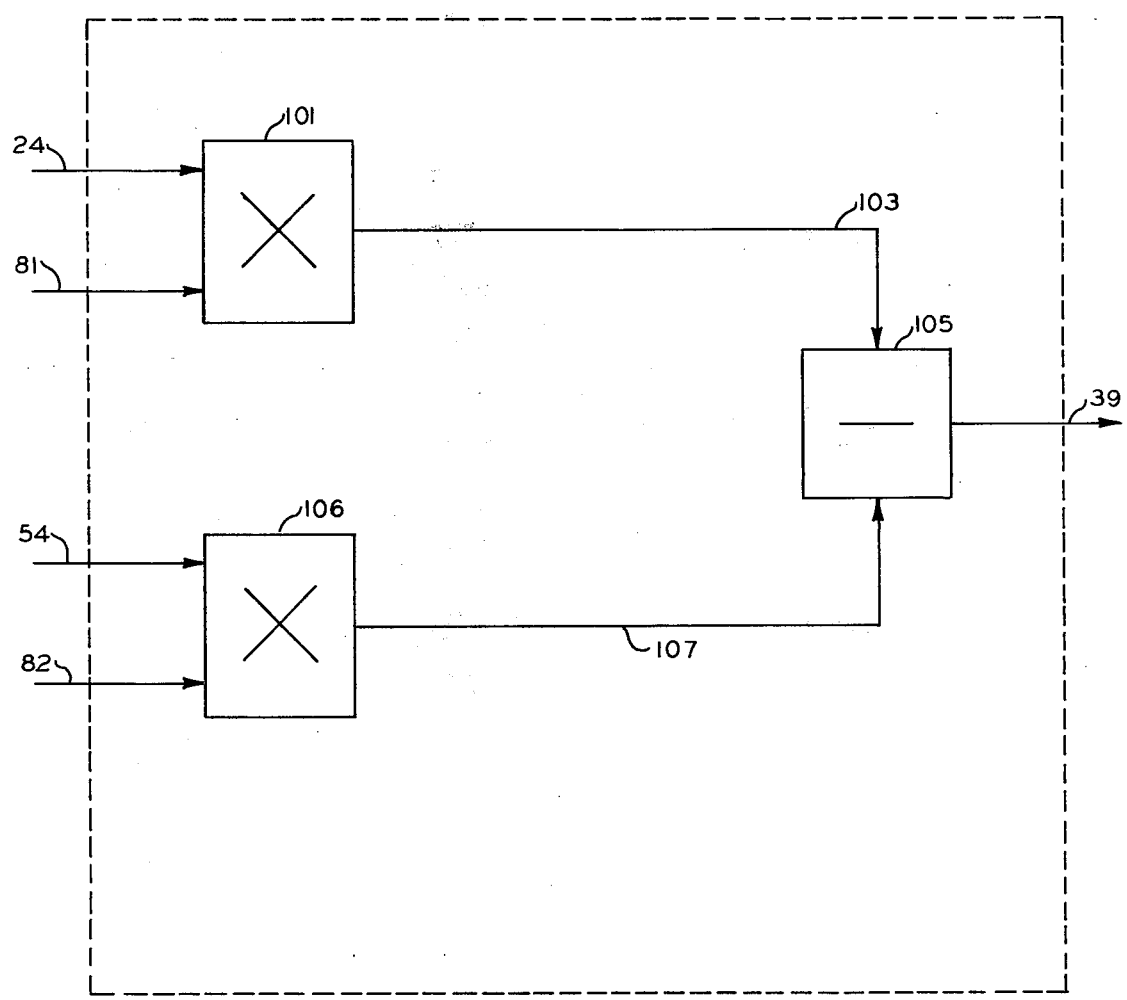

Other objects and advantages of the invention will be apparent from the description of the invention and the appended claims as well as from the detailed description of the drawings in which:

FIG. 1 is a representation of two chromatographic analyzer systems and a computer means; and FIG. 2 is a representation of the computer logic utilized in the invention.

The invention is described in terms of a specific chromatographic analyzer system and a refractive index detector. The invention is, however, applicable to other chromatographic analyzer systems and configurations and is also applicable to other types of detectors such as thermal conductivity detectors or dielectric constant detectors. The invention is described in terms of two separate chromatographic analyzer systems but one chromatographic analyzer system could be utilized if desired.

Referring now to the drawings and in particular to FIG. 1, there is shown two chromatographic columns 9 and 31. A sample of a fluid to be analyzed is delivered to sample valve 13 through conduit means 14. A conduit means 15 extends between sample valve 13 and the inlet to chromatographic column 11. A conduit means 16 extends between the outlet of chromatographic column 11 and the first inlet of a refractive index detector means 17. Carrier fluid is passed through the reference portion of the refractive index detector means 17 by being introduced into the second inlet of the refractive index detector means 17 through conduit means 18 which communicates with conduit means 12. Carrier fluid also flows through sample valve 13 and chromatographic column 11 to the first inlet of the refractive index detector means 17. At the beginning of an analysis period, sample valve 13 is actuated to introduce a predetermined volume of sample into the carrier fluid flowing through chromatographic column 11. The constituents of the sample are eluted in sequence and flow from chromatographic column 11 through conduit means 16 to the sample portion of the refractive index detector means 17. The refractive index detector means 17 establishes a signal 24, representative of a chromatographic analyzer output signal or response. Signal 24 is provided to a recorder means 25 and is also provided as one input to computer means 35.

In a manner identical to that described above, a second carrier fluid, different from the carrier fluid of conduit 12, is introduced through conduit means 42 to sample valve 43. A sample of the fluid to be analyzed is delivered to sample valve 43 through conduit means 44 which is operatively connected to conduit means 14. A conduit means 45 extends between sample valve 43 and the inlet to chromatographic column 31. A conduit means 46 extends between the outlet of chromatographic column 31 and the first inlet of a second refractive index detector means 47. Carrier fluid is passed through the reference portion of the refractive index detector means 47 by being introduced into the second inlet of the refractive index detector means 47 through conduit means 48 which communicates with conduit means 42. Carrier fluid also flows through sample valve 43 and chromatographic column 31 to the first inlet of the refractive index detector means 47. At the beginning of an analysis period, sample valve 43 is actuated to introduce a predetermined volume of sample into the carrier fluid flowing through chromatographic column 31. The constituents of the sample are eluted in sequence and flow from chromatographic column 31 through conduit means 46 to the sample portion of the refractive index detector means 17. The refractive index detector means 47 establishes a signal 54, representative of a chromatographic analyzer output signal or response. Signal 54 is supplied to a recorder means 55 and is also supplied as a second input to computer means 35.

Computer means 35 is also supplied with signals 81 and 82 which are representative of constants $k_3$ and $k_4$, previously defined in equation IX, respectively. Signals 24, 54, 81 and 82 are processed by computer means 35 to produce an output signal 39 which is representative of a quantitative measurement of the concentration of the individual constituents of the sample.

As has been previously stated, the first carrier fluid introduced through conduit means 12 to sample valve 13 and the second carrier fluid introduced through conduit means 42 to sample valve 43 are different from each other and have differing indexes of refraction. The two carrier fluids are chosen in such a manner that the sample components will be eluted in the same length of time. If this is not possible, then the carrier fluids are chosen in such a manner that the components of interest in the sample are completely resolved in both chromatographic analyzer output signals. If the second criteria is used, then the peak area is the parameter measured on both chromatograms.

The constants $k_3$ and $k_4$ may be established by using a solution which has a known concentration of two components. A first sample of the solution is introduced through sample valve 13 to the chromatographic column 9 and the response of the chromatographic analyzer to a first component, which is represented by signal 24, is recorded. The response of the chromatographic analyzer to a second component is also recorded. A second sample of the solution, which is identical to the first sample of the solution, is introduced through sample valve 43 to the chromatographic column 31. Again the chromatographic analyzer response, which is represented by signal 54, is recorded for both the first component and the second component.

The concentration of the first component is given by equation IX as $$C_1 = k_3 R_1 + k_4 R_2 \qquad \text{(XII)}$$

where $C_1$ is the concentration of the first component.
The concentration of the second component is given by equation IX as $$C_2 = k_3 R_1 + k_4 R_2 \qquad \text{(XIII)}$$

where $C_2$ is the concentration of the second component. $C_1$ and $C_2$ are known, therefore, there are two equations with two unknowns. $k_3$ and $k_4$ can be easily solved for and these constants will not change as long as the same two carrier fluids are utilized.

After the constants $k_3$ and $k_4$ have been calculated, a first sample is introduced through sample valve 13 to the chromatographic column 9 and the response of the chromatographic analyzer which is represented by signal 24 is recorded and is supplied as one input to computer means 35. A second sample which is identical to the first sample is introduced through sample valve 43 to chromatographic column 31. Again the chromatographic analyzer response which is represented by signal 54 is recorded and is provided as a second input to computer means 35. The chromatographic analyzer response represented by signal 24 and the chromatographic analyzer response represented by signals 54 are processed by computer means 35 to produce signal 39 which is representative of a quantitative analysis of the concentration of the individual constituents in the sample.

The processing of the chromatographic analyzer response represented by signal 24 and the chromatographic analyzer response represented by signal 54 may be accomplished by either an analog or a digital computer means. The functions performed by computer means 35 are illustrated in FIG. 2. Signals 24 and 81 are supplied as inputs to multiplying means 101. Signal 103, which is representative of $k_3 R_1$, is supplied from multiplying means 101 as a first input to subtracting means 105. In a similar manner signals 54 and 82 are supplied as inputs to multiplying means 106 and signal 107, representative of $k_4 R_2$, is supplied as a second input to the subtracting means 105. Signal 107 is subtracted from signal 103 in subtracting means 105 to produce signal 39 which is representative of a quantitative analysis of the concentration of the individual constituents of the sample.

If only a single chromatographic analyzer system were being utilized, it would be necessary to run only one sample, having a known concentration of an individual component, in two different carrier fluids. The constant k could be calculated directly from equation XI. A quantitative analysis could then be performed in the same manner as previously described except that a single chromatographic analyzer column would be utilized. As is shown in equation XI it would be necessary to subtract the separate response of the chromatographic analyzer system and then divide the difference between the responses by the constant k to provide a quantitative analysis of the concentration of the individual constituents of the sample.

The invention has been described in terms of a preferred embodiment as illustrated in FIGS. 1 and 2. As has been previously stated, many different chromatographic analyzer configurations could be utilized and also many different methods for analyzing the responses of the two chromatographic analyzer systems illustrated in FIG. 1 could be utilized to solve for the concentration of the individual components in the sample. The calculations could be performed by hand or a digital computer could be easily programmed to perform the required calculations. Also, a simple analog configuration could be utilized to perform the required calculations. If an analog computer is used, the subtracting means 105 and the multiplying means 101 and 106 could be a number B05885 Multiuse Amp, manufactured by Applied Automation Inc., Bartlesville, Oklahoma.

While the invention has been described in terms of the presently preferred embodiment, reasonable variations and modifications are possible by those skilled in the art, within the scope of the described invention and the appended claims. For instance, a thermal conductivity detector could be used in place of the refractive index detectors with the thermal conductivity of the carrier fluid and the sample being the parameter measured rather than the index of refraction. Also a single chromatographic analyzer system could be utilized as has been described.

That which is claimed is:

1. Apparatus for obtaining an analysis of the concentration of at least one individual component of a material comprising:

a chromatographic separation column means;

means for passing a first stream of a first carrier fluid to said chromatographic separation column means at a time $t_1$ and for passing a first stream of a second carrier fluid to said chromatographic separation column means at a time $t_2$, said first carrier fluid being different from said second carrier fluid, said time $t_2$ being later in time than said time $t_1$;

means for injecting a first sample of said material into the first stream of said first carrier fluid flowing to said chromatographic separation column means and for injecting a second sample of said material into the first stream of said carrier fluid flowing to said chromatographic separation column means;

a detector means capable of measuring a property of a fluid which is characteristic of the fluid;

means for passing the first stream of said first carrier fluid containing separated components of said first sample of said material from said chromatographic separation column means to said detector means as a sample stream and means for passing a second stream of said first carrier fluid to said detector means as a reference stream, said detector means providing a first signal representative of the response $R_1$ of said detector means when said first stream of said first carrier fluid containing separated components of said first sample and said second stream of said first carrier fluid are provided to said detector means;

means for passing the first stream of said second carrier fluid containing separated components of said second sample of said material from said chromatographic separation column means to said detector means as a sample stream and means for passing a second stream of said carrier fluid to said detector means as a reference stream, said detector means providing a second signal representative of the response $R_2$ of said detector means when said first stream of said second carrier fluid containing separated components of said second sample and said second stream of said second carrier fluid are provided to said detector means;

means for establishing a third signal k, which is a constant dependent on said property of said first carrier fluid, said property of said second carrier fluid, and the sensitivity of said detector means; and means for producing a fourth signal in response to said first signal, said second signal, and said third signal, said fourth signal being representative of the concentration of said at least one individual component of said material.

2. Apparatus in accordance with claim 1 wherein said means for producing said fourth signal comprises:

means for comparing said first signal and said second signal and for establishing a fifth signal representative of the difference between said first signal and said second signal; and means for dividing said fifth signal by said third signal to produce said fourth signal.

3. Apparatus in accordance with claim 1 wherein said detector means is a refractive index detector means.

4. Apparatus in accordance with claim 1 wherein said detector means is a thermal conductivity detector means.

5. Apparatus in accordance with claim 1 wherein said detector means is a dielectric constant detector means.

6. Apparatus for obtaining an analysis of the concentration of at least one individual component of a material comprising:

a first chromatographic separation column means;

means for passing a first stream of a first carrier fluid to said first chromatographic separation column means;

means for injecting a first sample of said material into the first stream of said first carrier fluid flowing to said first chromatographic separation column means;

a first detector means capable of measuring a property of a fluid which is characteristic of the fluid;

means for passing the first stream of said first carrier fluid containing separated components of said first sample of said material from said first chromatographic separation column means to said first detector means as a sample stream and means for passing a second stream of said first carrier fluid to said first detector means as a reference stream, said first detector means providing a first signal representative of the response $R_1$ of said first detector means;

a second chromatographic separation column means;

means for passing a first stream of a second carrier fluid to said second chromatographic separation column means, said first carrier fluid being different from said second carrier fluid;

means for injecting a second sample of said material into the first stream of said second carrier fluid flowing to said second chromatographic separation column means;

a second detector means capable of measuring said property;

means for passing the first stream of said second carrier fluid containing separated components of said second sample of said material from said second chromatographic separation column means to said second detector means as a sample stream and means for passing a second stream of said second carrier fluid to said second detector means as a reference stream, said second detector means providing a third signal representative of the response $R_2$ of said second detector means;

means for establishing a third signal $k_3$, which is a constant dependent on said property of said first carrier fluid, said property of said second carrier fluid, and the sensitivity of said first detector means;

means for establishing a fourth signal $k_4$, which is a constant dependent on said property of said first carrier fluid, said property of said second carrier fluid, the sensitivity of said first detector means, and the sensitivity of said second detector means; and means for producing a fifth signal in response to said first signal, said second signal, said third signal and said fourth signal, said fifth signal being representative of the concentration of said at least one individual component in said material.

7. Apparatus in accordance with claim 6 wherein said means for producing said fifth signal comprises:
   means for multiplying said first signal and said third signal to establish a sixth signal representative of $R_1 k_3$;
   means for multiplying said second signal and said fourth signal to establish a seventh signal representative of $R_2 k_4$; and
   means for subtracting said seventh signal from said sixth signal to establish said fifth signal.

8. Apparatus in accordance with claim 7 wherein said first detector means and said second detector means are refractive index detector means.

9. Apparatus in accordance with claim 7 wherein said first detector means and said second detector means are thermal conductivity detector means.

10. Apparatus in accordance with claim 7 wherein said first detector means and said second detector means are dielectric constant detector means.

11. A method for obtaining an analysis of the concentration of at least one individual component of a material comprising the steps of:
    performing a chromatographic analysis on said at least one individual component from a first sample of said material to obtain a first signal representative of a first response $R_1$, said at least one individual component from said first sample of said material being carried in a first carrier fluid;
    performing a chromatographic analysis on said at least one individual component from a second sample of said material to obtain a second signal representative of a second response $R_2$, said at least one individual component from said second sample of said material being carried in a second carrier fluid, said first carrier fluid being different from said second carrier fluid;
    establishing a third signal k, which is a constant dependent on said first carrier fluid, said second carrier fluid, and the sensitivity of said chromatographic analysis;
    producing a fourth signal in response to said first signal, said second signal, and said third signal, said fourth signal being representative of the concentration of said at least one individual component in said material.

12. A method in accordance with claim 11 wherein said step of producing said fourth signal comprises:
    subtracting said second signal from said first signal to establish a fifth signal; and
    dividing said fifth signal by said third signal to establish said fourth signal.

13. A method for obtaining an analysis of the concentration of at least one individual component of a material comprising the steps of:
    performing a first chromatographic analysis on said at least one individual component from a first sample of said material to obtain a first signal representative of a first response $R_1$, said at least one individual component from said first sample of said material being carried in a first carrier fluid;
    performing a second chromatographic analysis on said at least one individual component from a second sample of said material to obtain a second signal representative of a second response $R_2$, said at least one individual component from said second sample of said material being carried in a second carrier fluid, said first carrier fluid being different from said second carrier fluid;
    establishing a third signal $k_3$, which is a constant dependent on said first carrier fluid, said second carrier fluid, and the sensitivity of said first chromatographic analysis;
    establishing a fourth signal $k_4$, which is a constant dependent on said first carrier fluid, said second carrier fluid, the sensitivity of said first chromatographic analysis, and the sensitivity of said second chromatographic analysis; and
    producing a fifth signal in response to said first signal, said second signal, said third signal, and said fourth signal, said fifth signal being representative of the concentration of said at least one individual component in said material.

14. A method in accordance with claim 13 wherein said step of producing said fifth signal comprises:
    multiplying said first signal and said third signal to establish a sixth signal representative of $R_1 k_3$;
    multiplying said second signal and said fourth signal to establish a seventh signal representative of $R_2 k_4$; and
    subtracting said seventh signal from said sixth signal to establish said fifth signal.

* * * * *

UNITED STATES PATENT AND TRADEMARK OFFICE
CERTIFICATE OF CORRECTION

PATENT NO. : 4,181,006
DATED : January 1, 1980
INVENTOR(S) : Donald D. DeFord

It is certified that error appears in the above-identified patent and that said Letters Patent are hereby corrected as shown below:

Column 7, claim 1, lines 26 and 48, after "said" and before
        "carrier", insert --- second ---.

Signed and Sealed this

Thirtieth Day of September 1980

[SEAL]

Attest:

SIDNEY A. DIAMOND

Attesting Officer     Commissioner of Patents and Trademarks